US00PP07786P

United States Patent [19]

Danziger

[11] Patent Number: Plant 7,786

[45] Date of Patent: Feb. 11, 1992

[54] ASTER PLANT NAMED DARK PINK STAR

[76] Inventor: Micha Danziger, Post Beit Dagan, P.O.B. 24, Moshav Mishmar Hashiva 50 297, Israel

[21] Appl. No.: 604,224

[22] Filed: Oct. 29, 1990

[51] Int. Cl.[5] ..... A01H 5/00
[52] U.S. Cl. ..... Plt./68
[58] Field of Search ..... Plt./68

*Primary Examiner*—James R. Feyrer

*Attorney, Agent, or Firm*—Foley & Lardner

[57] ABSTRACT

An Aster plant named Dark Pink Star particularly characterized by its cupped capitulum form; single daisy capitulum type; purple ray floret color; bright yellow disk florets; diameter across face of capitulum of 24 to 27 mm at maturity; strong, well branched flower stems; stems with anthocyanin, and many capitula per inflorescence on short pedicels.

1 Drawing Sheet

The present invention comprises a new and distinct cultivar of Aster plant, botanically known as *Aster ericoides,* and hereinafter referred to by the cultivar name Dark Pink Star.

Dark Pink Star is a naturally occurring mutation and was discovered by the inventor Micha Danziger as one flowering plant within a block of flowering plants of the parent cultivar Pink Star (*Aster ericoides*) in a controlled growing environment in Mishmar Hashiva, Israel. The mutation was recognized primarily by its darker, more intense pink flower color, and its darker leaves. There are further differences between the new cultivar and its parent, and these are mentioned below.

The first act of asexual reproduction of Dark Pink Star was accomplished when vegetative cuttings were taken from the mutation in a controlled environment in Mishmar Hashiva, Israel by the inventor. Subsequent horticultural examination of selected plants of Dark Pink Star has demonstrated that the unique combination of characteristics as herein disclosed for Dark Pink Star are firmly fixed and are retained through successive generations of asexual reproduction.

Dark Pink Star has not been observed under all possible environmental conditions. The phenotype may vary significantly with variations in environment such as temperature, light intensity and daylength.

The following observations, measurements and comparisons describe plants grown in Mishmar Hashiva, Israel under growing conditions which approximate those generally used in commercial practice.

The following traits have been repeatedly observed and are determined to be basic characteristics of Dark Pink Star, which, in combination, distinguish this Aster as a new and distinct cultivar:

1. Cupped capitulum form.
2. Single daisy capitulum type.
3. Medium purple ray floret color.
4. Large cushion of bright yellow disc florets, which pleasantly contrast with the purple ray florets.
5. Diameter across face of fully open capitulum of approximately 24–27 mm. at maturity.
6. Strong, well branched flower stems.
7. Many capitula per inflorescence on short pedicels.
8. The stems contain anthocyanin, the amounts of which are greater just before flowering.
9. Medium size, dark green foliage.
10. Early blooming.

The accompanying photographic drawings show typical inflorescence of Dark Pink Star, with the colors being as nearly true as possible with illustrations of this type. The color photograph at the top of the drawing sheet is a perspective view of Dark Pink Star grown as a single stem cut spray Aster. The color photograph at the bottom of the sheet is an enlarged closeup of a typical flower of Dark Pink Star, with the flower being slightly greater than double its actual size.

Of the cultivars known to the inventor, the most similar in comparison to Dark Pink Star is the parent Pink Star. In comparison to Pink Star, Dark Pink Star has a darker, more intense flower color, its flower stems contain anthocyanin in increasing amounts just before flowering, its foliage is darker, it has an earlier blooming, and its flower structure is different. The last mentioned characteristic is in reference to Dark Pink Star's smaller flower diameter but greater number of petals. The earlier blooming characteristic is particularly evident in the winter when the parent Pink Star needs a longer period of long days and also greater light intensity for both elongation and for producing a commercially sufficient number of buds.

In the following description color references are made to The Royal Horticultural Society Color Chart, and were determined at Mishmar Hashiva, Israel during both winter and summer conditions.

Classification:

*Botanical.*—*Aster ericoides* cv Dark Pink Star.
*Commercial.*—Small daisy-like spray Aster.

INFLORESCENCE

A. Capitulum:
*Form.*—Cupped.
*Type.*—Daisy.
*Diameter across face.*—2.4–2.7 cm.

B. Corolla of ray florets:
*Color (general tonality from a distance of three meters).*—Medium purple.
*Color (upper surface).*—Closest to 77B at opening, in both winter and summer. There is some color fading in high light intensity periods in the summer.
*Color (under surface).*—Closest to 77B.
*Shape of floret.*—Apex rounded; narrow, oblong, straight to slightly concave.

*Size of floret.*—10–13 mm. long×2.3 mm. wide.
*Number of ray florets.*—27–30.

C. Corolla of disc florets:
*Color (mature).*—Closest to 7A.
*Color (immature).*—Closest to 13A to 13B.
*Diameter of disc.*—7–8 mm.

D. Flowering period: When field grown in natural season, plants planted in June will flower in September. In winter greenhouse production, preferred culture includes long day treatment after pinching until the stems elongate to approximately 10 cm., followed by short days until flower induction.

E. Reproductive organs:
*Androecium.*—Stamens present on both ray and disc florets; pollen is found only in the winter season (in Israel).
*Gynoecium.*—Present on both ray and disc florets.

PLANT

A. General appearance:
*Height.*—Medium to tall; depends on light conditions; good branching.

B. Foliage:
*Color.*—139A-B.
*Shape.*—Linear, with occasional downward reflexing at the tip.
*Size.*—Typically 12 cm. long and 1.5 cm. wide.
*Margin.*—Entire.
*Arrangement.*—Alternate, with angle acute.

I claim:

1. A new and distinct Aster plant named Dark Pink Star, as described and illustrated.

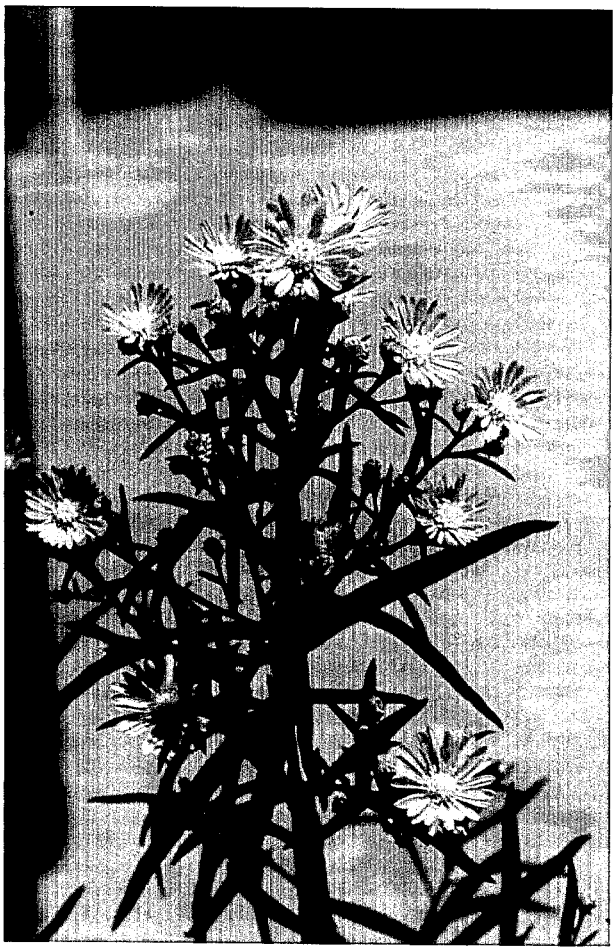
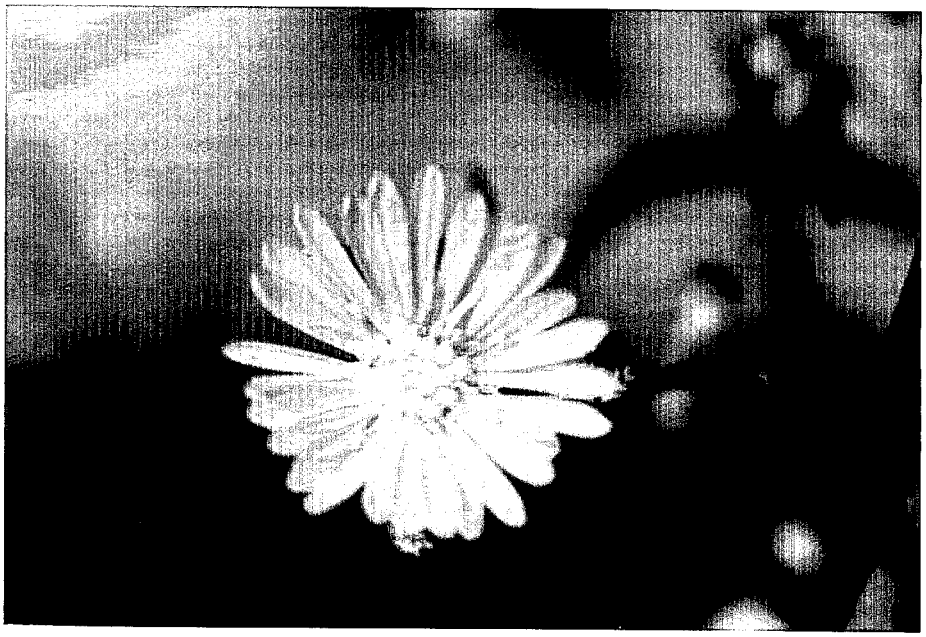

* * * * *